(12) United States Patent
Reddy et al.

(10) Patent No.: US 8,173,817 B2
(45) Date of Patent: *May 8, 2012

(54) STEREOSELECTIVE SYNTHESIS OF BENZIMIDAZOLE SULFOXIDES

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN)

(73) Assignee: Hetero Drugs Limited (IN)

( * ) Notice: Subject to any disclaimer, the term of this patent is extended or adjusted under 35 U.S.C. 154(b) by 1043 days.

This patent is subject to a terminal disclaimer.

(21) Appl. No.: 11/865,312

(22) Filed: Oct. 1, 2007

(65) Prior Publication Data

US 2008/0076930 A1  Mar. 27, 2008

Related U.S. Application Data

(62) Division of application No. 10/503,846, filed on Aug. 6, 2004, now Pat. No. 7,365,206.

(51) Int. Cl.
  *C07D 401/12* (2006.01)
(52) U.S. Cl. .................................. 546/273.7
(58) Field of Classification Search ............... 546/273.7
  See application file for complete search history.

(56) References Cited

U.S. PATENT DOCUMENTS

| | | | |
|---|---|---|---|
| 4,738,974 A | 4/1988 | Brandstrom | |
| 5,714,504 A | 2/1998 | Lindberg | |
| 5,877,192 A | 3/1999 | Lindberg | |
| 5,948,789 A | 9/1999 | Larsson | |
| 6,559,167 B1 | 5/2003 | Garst | |
| 7,435,826 B2 * | 10/2008 | Reddy et al. | 546/273.7 |

FOREIGN PATENT DOCUMENTS

| | | |
|---|---|---|
| DE | 4035455 | 5/1992 |
| EP | 5129 | 10/1979 |
| EP | 221041 | 5/1987 |
| WO | WO 9427988 | 12/1994 |
| WO | WO 2004002982 | 1/2004 |

OTHER PUBLICATIONS

Sigrist-Nelson K, Krasso A, Muller RK, Fischli AE. Ro 18-5364, a potent new inhibitor of the gastric (H+ + K+)-ATPase. Eur J Biochem. Jul. 15, 1987;166(2):453-9.

PCT International Search Report Dated May 28, 2004.

* cited by examiner

*Primary Examiner* — Patricia Morris

(74) *Attorney, Agent, or Firm* — Caesar, Rivise, Bernstein, Cohen & Pokotilow, Ltd.

(57) ABSTRACT

The present invention relates to a process for stereoselective synthesis of substituted sulfoxides either as a single enantiomer or in an enantiomerically enriched form. Thus, 5-methoxy-2-[[(4-methoxy-3,5-dimethyl-2-pyridinyl)methyl]thio]-1H-benzimidazole is reacted with (R)-camphorsulfonyl chloride to form a mixture of 1-(R)-camphorsulfonyl-5- (and 6-)methoxy-2-[(3,5-dimethyl-4-methoxy-2-pyridyl)methylthio]-1H-benzimidazole, oxidized to obtain a diastereomeric excess of 1-(R)-camphorsulfonyl-(5- and 6-)-methoxy-2-[(3,5-dimethyl-4-methoxy-2-pyridyl)methyl-(S)-sulfinyl]-1H-benzimidazole over 1-(R)-camphorsulfonyl-(5- and 6-)-methoxy-2-[(3,5-dimethyl-4-methoxy-2-pyridyl)methyl-(R)-sulfinyl]-1H-benzimidazole, the diastereomers are separated by fractional crystallization and the separated 1-(R)-camphorsulfonyl-(5- and 6-)-methoxy-2-[(3,5-dimethyl-4-methoxy-2-pyridyl)methyl-(S)-sulfinyl]-1H-benzimidazole is deprotected to give esomeprazole.

19 Claims, No Drawings

STEREOSELECTIVE SYNTHESIS OF BENZIMIDAZOLE SULFOXIDES

This application is a Divisional of U.S. patent application Ser. No. 10/503,846, filed Aug. 6, 2004 now U.S. Pat. No. 7,365,206, which is a National Stage Entry of PCT/IN04/00143, filed May 28, 2004, the entire disclosures of which are incorporated by reference herein in their entireties.

FIELD OF THE INVENTION

The present invention relates to a process for stereoselective synthesis of benzimidazole sulfoxides either as a single enantiomer or in an enantiomerically enriched form.

BACKGROUND OF THE INVENTION

Substituted 2-(2-pyridinylmethylsulfinyl)-1H-benzimidazoles such as for example omeprazole, pantoprazole, lansoprazole and rabeprazole including their stereoisomers are inhibitors of gastric acid secretion. Omeprazole, chemically 5-methoxy-2-[[(4-methoxy-3,5-dimethyl-2-pyridinyl)methyl]sulfinyl]-1H-benzimidazole is for instant disclosed in EP 5129. Some compounds useful as prodrugs of proton pump inhibitors are disclosed in U.S. Pat. No. 6,559,167.

The alkaline salts of (S)-enantiomer of omeprazole (esomeprazole), the pharmaceutical preparations of these salts and the method of treatment of gastric acid-related diseases using them are disclosed in U.S. Pat. Nos. 4,738,974, 5,877,192 and 5,714,504. The patents U.S. Pat. Nos. 4,738,974, 5,877,192 and 5,714,504 are incorporated herein by reference.

These compounds and structurally related compounds have a stereogenic center at sulfur and therefore exist as two optical isomers. The resolution processes of racemates of these compounds were for example disclosed in DE 4035455 and WO 94/27988. According to these processes chiral ether such as fenchyloxymethyl or chiral acyloxy methyl group such as mandeloyl- is introduced into the 1-position of benzimidazole ring of racemic sulfoxide compound to obtain a diastereomeric mixture, diastereomers are then separated and desired isomer is liberated from a separated diastereomer. The process requires either the preparation of fenchyloxymethyl chloride and then reaction with the racemic compound; or introduction of chloromethyl group on 1-position of benzimidazole ring, followed by reaction with the chiral auxiliary. We find that these intermediates are difficult to prepare and involve in many steps.

The resolution of sulfoxide compounds including racemic omeprazole were described in WO 2004/002982. The method requires expensive reagents like titanium compounds, two chiral reagents namely diethyl-D-tartarate and L-Mandelic acid.

Enantioselective synthesis is described for example in Euro. J. Biochem. 166 (1987) 453 and U.S. Pat. No. 5,948,789. Disadvantages of these methods are that strict control of conditions is to be maintained and strict control of quantities of oxidizing agents is required for avoiding oxidation of desired sulfoxide to sulfone impurity. Moreover, these methods require expensive reagents like titanium isoproxide and diethyl-D-tartarate.

The process for the preparation of racemic benzimidazole sulfoxides such as omeprazole, useful as starting materials for preparing enantiomerically pure benzimidazole sulfoxides, from their corresponding sulfides involves a problem of over oxidation to form sulfone impurities.

PCT Application No. PCT/IN04/00118 describes the resolution method for racemic benzimidazole sulfoxides.

We have discovered a novel process for preparing benzimidazole sulfoxides either as a single enantiomer or in an enantiomerically enriched form using less expensive reagents. The novel method provides a commercially viable stereoselective synthesis of benzimidazole sulfoxides. The novel process provides an excess amount of the desired enantiomer of benzimidazole sulfoxides over the undesired enantiomer. This results in the improved overall yield of optically pure or optically enriched benzimidazole sulfoxides.

Some of the intermediates of the process are novel and also the part of the invention.

SUMMARY OF THE INVENTION

The present invention provides a stereoselective synthesis for preparing a benzimidazole sulfoxide of formula I or a salt thereof either as a single enantiomer or in an enantiomerically enriched form:

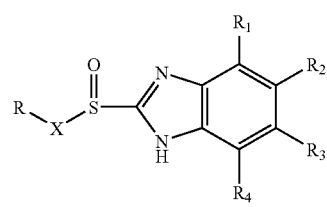

I

Wherein
R is

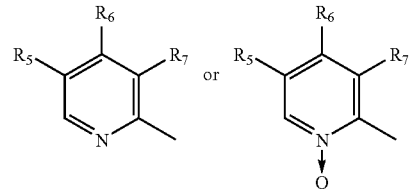

X is

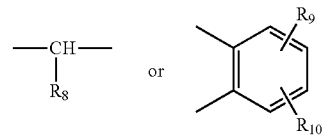

and $R_1$-$R_4$ are the same or different and selected from hydrogen, alkyl, alkoxy, halogen, halo-alkoxy, alkylcarbonyl, alkoxycarbonyl, oxazolyl, trifluoroalkyl, or adjacent groups $R_1$-$R_4$ form ring structures which may be further substituted; wherein $R_5$ and $R_7$ are same or different and selected from hydrogen, alkyl, alkylthio, alkoxy optionally substituted by fluorine, alkoxyalkoxy, dialkylamino, piperidino, morpholino, halogen, phenylalkyl and phenylalkoxy;

$R_6$ is selected from hydrogen, alkyl, alkylthio, alkoxy optionally substituted by fluorine, alkoxyalkoxy, dialkylamino, piperidino, morpholino, halogen, nitro, phenylalkyl and phenylalkoxy;

$R_8$ is hydrogen or forms an alkylene chain together with $R_7$ and $R_9$ and $R_{10}$ are same or different and selected from hydrogen, halogen and alkyl;

which comprises:

a) reacting a benzimidazole sulfide of formula II, or a salt thereof:

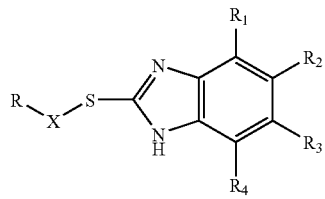

wherein R, X and $R_1$-$R_4$ are as defined for formula I;
with a chiral compound of formula III:

$$R^C-Z-Y \qquad\qquad III$$

wherein $R^C$ is a chiral moiety having at least one asymmetric center and at least one asymmetric center in the chiral moiety can have either R or S configuration;
Z is

and Y is a leaving group
to provide a compound of formula IV:

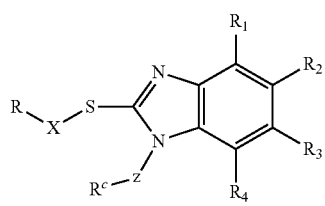

wherein R, X and $R_1$-$R_4$ are as defined for formula I; and $R^C$ and Z are as defined for formula III;

b) oxidizing the compound of formula IV to give a diastereomeric excess of compound of formula V:

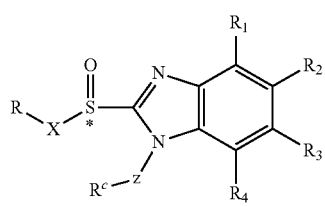

wherein R, X, $R^C$, $R_1$-$R_4$ and Z are as defined for formula IV and star (*) refers to excess of one configuration at the sulfur atom of the sulfoxide group over the opposite configuration;

c) if required, separating the diastereomers of formula V; and d) deprotecting the product of step (b); or separated diastereomers of step (c) with an acid or base to provide a single enantiomer or enantiomerically enriched compound of formula I and optionally converting the enantiomer formed to the salt.

In the above definitions alkyl groups, alkoxy groups and moieties thereof may be branched or straight $C_1$-$C_9$-chains or comprise cyclic alkyl groups, for example cyclicalkylalkyl.

Some of the intermediates of the process are novel and also the part of the invention.

DETAILED DESCRIPTION OF THE INVENTION

The present invention provides a stereoselective synthesis for preparing a benzimidazole sulfoxide of formula I or a salt thereof either as a single enantiomer or in an enantiomerically enriched form:

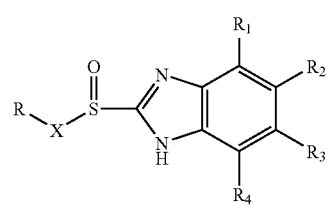

Wherein
R is

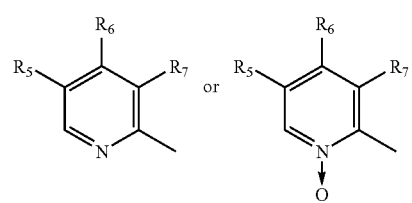

X is

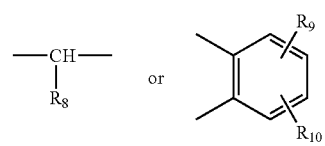

and $R_1$-$R_4$ are the same or different and selected from hydrogen, alkyl, alkoxy, halogen, halo-alkoxy, alkylcarbonyl, alkoxycarbonyl, oxazolyl, trifluoroalkyl, or adjacent groups $R_1$-$R_4$ form ring structures which may be further substituted;

wherein $R_5$ and $R_7$ are same or different and selected from hydrogen, alkyl, alkylthio, alkoxy optionally substituted by fluorine, alkoxyalkoxy, dialkylamino, piperidino, morpholino, halogen, phenylalkyl and phenylalkoxy;

$R_6$ is selected from hydrogen, alkyl, alkylthio, alkoxy optionally substituted by fluorine, alkoxyalkoxy, dialkylamino, piperidino, morpholino, halogen, nitro, phenylalkyl and phenylalkoxy;

$R_8$ is hydrogen or forms an alkylene chain together with $R_7$ and $R_9$ and $R_{10}$ are same or different and selected from hydrogen, halogen and alkyl.

Except otherwise states, alkyl groups, alkoxy groups and moieties thereof may be branched or straight $C_1$-$C_9$-chains or comprise cyclic alkyl groups, for example cyclicalkylalkyl.

The star (*) refers to excess of one configuration at the sulfur atom of the sulfoxide group over the other configuration.

Preferably, the sulfoxides prepared by the novel method are sulfoxides of formula I' or a salt thereof either as a single enantiomer or in an enantiomerically enriched form:

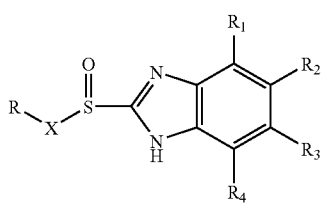

I'

Wherein R is

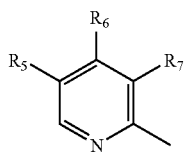

$R_6$ is selected from hydrogen, alkyl, alkylthio, alkoxy optionally substituted by fluorine, alkoxyalkoxy, dialkylamino, piperidino, morpholino, halogen, phenylalkyl and phenylalkoxy; and $R_1$-$R_5$, $R_7$-$R_{10}$ and X are as defined for formula I.

More preferably the sulfoxides prepared by the novel process are sulfoxides of any of the formulas I(i) to I(vi) or a salt thereof either as a single enantiomer or in an enantiomerically enriched form:

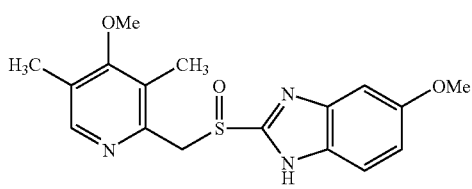

I(i)

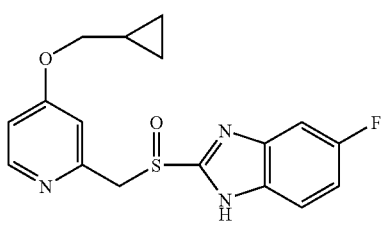

I(ii)

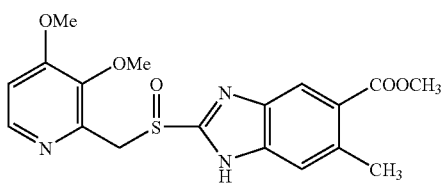

I(iii)

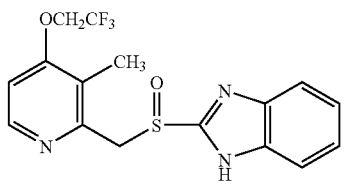

I(iv)

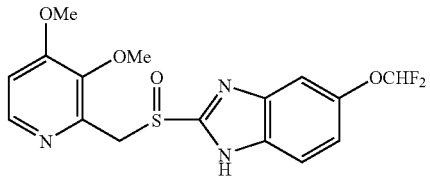

I(v)

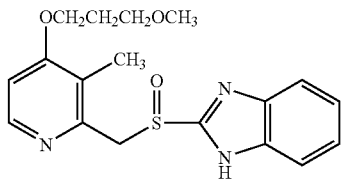

I(vi)

The compounds defined by the formulas I, I' and I(i-vi) may be converted to pharmaceutically acceptable salts by conventional methods.

Most preferably the sulfoxide prepared by the novel process is sulfoxide of the formula I(i) or a salt thereof either as a single enantiomer or in an enantiomerically enriched form.

According to the present invention initially a benzimidazole sulfide of formula II or a salt thereof:

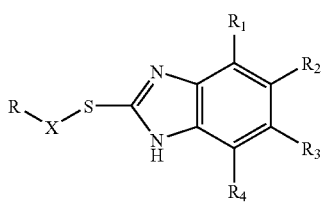

II is reacted with a chiral compound of formula III:

III to provide a compound of formula IV:

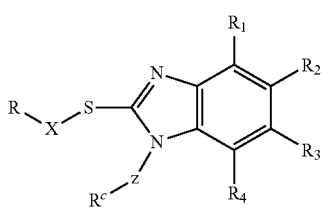

IV

In the formulas II-IV, R, X, and $R_1$-$R_4$ have the same meaning as defined for formula I; $R^C$ is a chiral moiety having at least one asymmetric center and at least one asymmetric center in the chiral moiety can have either R or S configuration; Z is

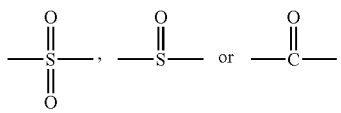

and Y is a leaving group such as halogen, hydroxy or reactive esterified hydroxy.

The salts of the compounds of formula II used in the reaction may be inorganic or organic salts. The preferable inorganic salts are alkali salts or alkaline earth metal salts. Preferred alkali metal salt of the compounds of formula II is lithium, sodium or potassium, more preferred being sodium or potassium metal salt. Preferred alkaline earth metal salt of the compounds of formula II is calcium or magnesium, more preferred being magnesium metal salt. The preferred organic salts of the compounds of formula II are organic ammonium salts, more preferred being tert-butylammonium salt, tetrabutylammonium salt and guanidinium salt.

The preferred Z is sulfonyl group:

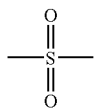

$R^C$ may or may not have aryl substitutions such as phenyl or hetero aryl substitutions such as pyridine on its chiral moiety. Preferably, $R^C$—Z— is selected from (S) or (R)-camphor sulfonyl, (S)- or (R)-glycidylsulfonyl-, D- or L-mandeloyl, a stereo isomeric 1-(ethoxycarbonyl)-3-phenylpropyl]alanyl, (D) or (L)-phenyl alanyl and (D) or (L)-alanyl.

Preferably, reactive esterified hydroxy group is acetoxy or trifluoroacetoxy.

Halogen represents F, Cl, Br or I.

Preferably, Y is halogen, more preferably Cl or Br, still more preferably Cl.

Preferably, the reaction between the benzimidazole sulfide of formula II and the optically active compound of formula III is carried out in a solvent. Suitable solvents that can be used are esters such as ethyl acetate, methyl acetate, isopropyl acetate, tert-butyl methyl acetate and ethyl formate; alcohols such as methanol, ethanol and isopropyl alcohol; acetonitrile; tetrahydrofuran; dimethylformamide; dimethylsulfoxide; dioxane; aromatic hydrocarbons such as benzene, toluene, xylene, etc.; halogenated hydrocarbons such as methylene chloride, chloroform, carbontetrachloride, ethylene dichloride, etc.; ketones such as acetone, methyl ethyl ketone, methyl isobutyl ketone, diethyl ketone etc.; ethers such as tert-butyl methyl ether, diethyl ether; diethyl carbonate and a mixture thereof. Preferable solvents are selected from halogenated hydrocarbon solvents and aromatic hydrocarbon solvents, still more preferred solvents are methylene chloride, ethylenedichloride, toluene, benzene and xylene.

Preferably the reaction is carried out in the presence of a base such as N,N-diisopropylethylamine, triethyl amine or sodium carbonate.

The compounds of a formula IV are novel and constitutes another aspect of the invention.

The compound of formula IV is oxidized to give diastereomeric excess of sulfoxide of formula V:

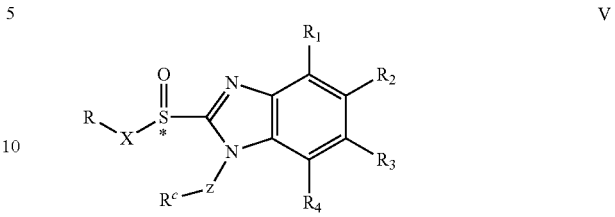

wherein R, X, $R^C$, $R_1$-$R_4$ and Z are as defined for formula IV.

By using a suitable chiral auxiliary $R^C$—Z—Y (formula III) for preparing the compound of formula IV, the desired diastereomer can be obtained in excess over the undesired diastereomers.

Any oxidizing agents that are known for oxidizing sulfide to sulfoxide can be used. The preferred oxidizing agents are nitric acid, hydrogen peroxide, peracids, peresters, ozone, dinitrogentetraoxide, iodosobenzene, N-halosuccinimide, 1-chlorobenzotriazole, t-butylhypochlorite, sodium hypochlorite, diazobicyclo-[2,2,2]-octane bromine complex, sodium metaperiodate, selenium dioxide, manganese dioxide, chromic acid, cericammonium nitrate, bromine, chlorine, and sulfuryl chloride. More preferred oxidizing agents are peracids such as peracetic acid and m-chloro perbenzoic acid; hydrogen peroxide, sodium hypochlorite and sodium metaperiodate. The oxidation can also be performed with the oxidizing agent in the presence of a catalyst such as vanadium acetyl acetonate.

Oxidation is carried out in a solvent or a mixture of solvents. The preferred solvents are esters such as ethyl acetate, methyl acetate, isopropyl acetate, tert-butyl methyl acetate and ethyl formate; carboxylic acid solvents such as acetic acid; alcohols such as methanol, ethanol and isopropyl alcohol; acetonitrile; tetrahydrofuran; dimethylformamide; dimethylsulfoxide; dioxane; aromatic hydrocarbons such as benzene, toluene, xylene, etc.; halogenated hydrocarbons such as methylene chloride, chloroform, carbontetrachloride, ethylene dichloride, etc.; ketones such as acetone, methyl ethyl ketone, methyl isobutyl ketone, diethyl ketone etc.; ethers such as tert-butyl methyl ether, diethyl ether; diethyl carbonate and a mixture thereof. More preferred solvents are selected from halogenated hydrocarbon solvents, carboxylic acid solvents and aromatic hydrocarbon solvents, still more preferred solvents are methylenedichloride, ethylenedichloride, acetic acid, toluene, benzene and xylene.

The diastereomeric excess refers to formation of a diastereomer having one configuration at sulfur of sulfoxide in excess over that having the opposite configuration. Preferably, one diastereomer is formed in above about 60% of the mixture of diastereomers over the other and more preferably, above about 80% of the mixture of diastereomers.

The compounds of formula V formed may be isolated from the reaction medium and then used in the next step; or used directly in the next step.

The compounds of formula V formed above can be separated and the separated diastereomers are deprotected; or used directly in the deprotection step. The separation of diastereomers may be required to obtain stereomers with desired optically purity. It is well known that diastereomers differ in their properties such as solubility and they can be separated based on the differences in their properties. The separation of the diastereomers can be performed using the methods known to the person skilled in the art. These methods include chromatographic techniques and fractional crystallization, preferable method being fractional crystallization.

Preferably, a solution of the diastereomeric mixture is subjected to fractional crystallization. The solution of the diastereomeric mixture may be a solution of the reaction mixture obtained as above or a solution prepared by dissolving the isolated diastereomeric mixture in a solvent. Any solvent may be used so long as it can be used for the separation. The preferred solvent is selected from alcohols such as methanol, ethanol and isopropyl alcohol, propanol, tert-butylalcohol, n-butanol; ketones such as acetone, methyl ethyl ketone, methyl isobutyl ketone, diethyl ketone; esters such as ethyl acetate, methyl acetate, isopropyl acetate, tert-butyl methyl acetate and ethyl formate; acetonitrile; tetrahydrofuran; dimethylformamide; dimethylsulfoxide; dioxane; diethyl carbonate and a mixture thereof. Water may also be associated with the above solvents. Preferable solvents are alcohol and ketone solvents, still more preferred solvents are alcohol solvents such as isopropyl alcohol and ethanol.

Fractional crystallization of preferentially one diastereomer from the solution of mixture of diastereomers can be performed by conventional methods such as cooling, partial removal of solvents, using contrasolvent, seeding or a combination thereof.

Fractional crystallization can be repeated until the desired chiral purity is obtained. But, usually one or two crystallizations may be sufficient.

The separated diastereomer of formula V or the compound of formula V without subjecting for separation is then deprotected to provide sulfoxide of formula I either as a single enantiomer or in an enantiomerically enriched form. The deprotection can be applied to the separated diastereomers to get respective enantiomers.

The single enantiomer or the enantiomerically enriched enantiomer can be isolated from the reaction mixture or it can be isolated as a salt. The salts of the sulfoxide enantiomers can be prepared by conventional means. Optionally the enantiomers or salts thereof can be converted into pharmaceutically acceptable salts by conventional methods.

The deprotection can be performed by using an acid or a base. The selection of the acid or base is not critical. The acid can be an organic or inorganic. Acids such as carboxylic acids, e.g. acetic acid, formic acid; sulfonic acids, e.g. methane sulfonic acid; mineral acids such as phosphoric acid can be used.

The deprotection is preferably carried out with a base. The base can be an organic or inorganic. Preferable organic base is an amine. The amine may be primary, secondary or tertiary amine. The more preferred amine is triethyl amine or N,N-diisopropylethylamine.

The preferable inorganic bases are hydroxides, carbonates, bicarbonates, alkoxides and oxides of alkali or alkaline earth metals. The preferred alkali metal compounds are those of lithium, sodium and potassium, more preferred being those of sodium and potassium. The preferred alkaline earth metal compounds are those of calcium and magnesium more preferred being those of magnesium. Some example of these bases are sodium hydroxide, potassium hydroxide, magnesium hydroxide, magnesium oxide, sodium carbonate, potassium carbonate, sodium bicarbonate, potassium bicarbonate, sodium tert.butoxide and potassium tert.butoxide. The more preferred bases are hydroxides of sodium and potassium.

The deprotection may be carried out by contacting the separated diastereomer or a salt thereof with the base preferably in the presence of a solvent.

Suitable solvents that can be used in the deprotection are esters such as ethyl acetate, methyl acetate, isopropyl acetate, tert-butyl methyl acetate and ethyl formate; alcohols such as methanol, ethanol and isopropyl alcohol; acetonitrile; tetrahydrofuran; dimethylformamide; dimethylsulfoxide; dioxane; aromatic hydrocarbons such as benzene, toluene, xylene, etc.; halogenated hydrocarbons such as methylene chloride, chloroform, carbontetrachloride, ethylene dichloride, etc.; ketones such as acetone, methyl ethyl ketone, methyl isobutyl ketone, diethyl ketone etc.; ethers such as tert-butyl methyl ether, diethyl ether; diethyl carbonate and a mixture thereof. Preferable solvents are alcohol and ketone solvents, still more preferred solvents are alcohol solvents such as methanol, isopropyl alcohol and ethanol.

The separation and deprotection methods of benzimidazole sulfoxides are described in application No. PCT/IN04/00118, which is herein incorporated by reference.

The enantiomers of compounds of formula I are either inhibitors of gastric acid secretion or intermediates for preparing them. These intermediates can be converted to the members of inhibitors of gastric acid secretion. For instant if $R_6$ of an enantiomer of the compound of formula I is nitro group then nitro can be replaced by methoxy group using sodium methoxide to obtain another member of the formula I. Similarly if R of an enantiomer of the compound of formula I is

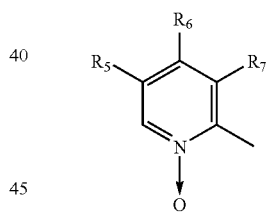

the N-oxide group can be reduced to pyridine compound by known methods to obtain another member of formula I.

The compounds of formula V as diastereomeric mixture or as individual diastereomers including their salts are novel and are also part of the invention.

(S)-5-Methoxy-2-[(3,5-dimethyl-4-methoxy-2-pyridyl) methylsulfinyl]1-H-benzimidazole ((S)-Omeprazole or Esomeprazole) or a salt thereof is the most preferred compound of the formula I. The preferred process for preparing esomeprazole or the salt can be shown in the scheme:

Scheme:
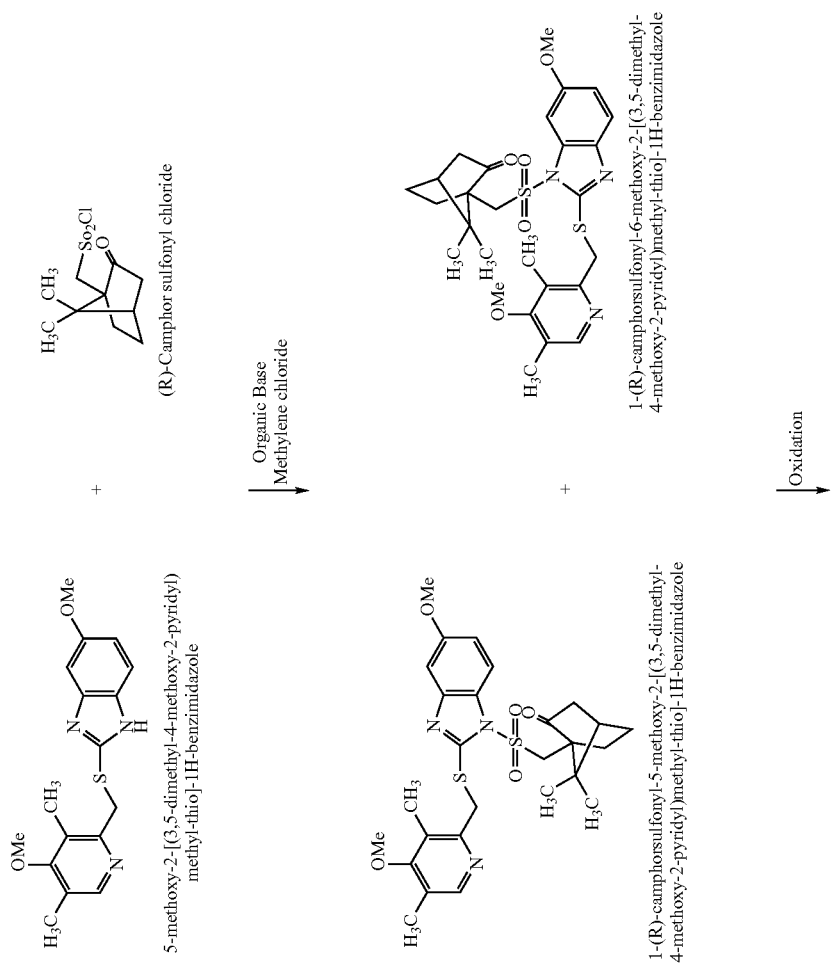

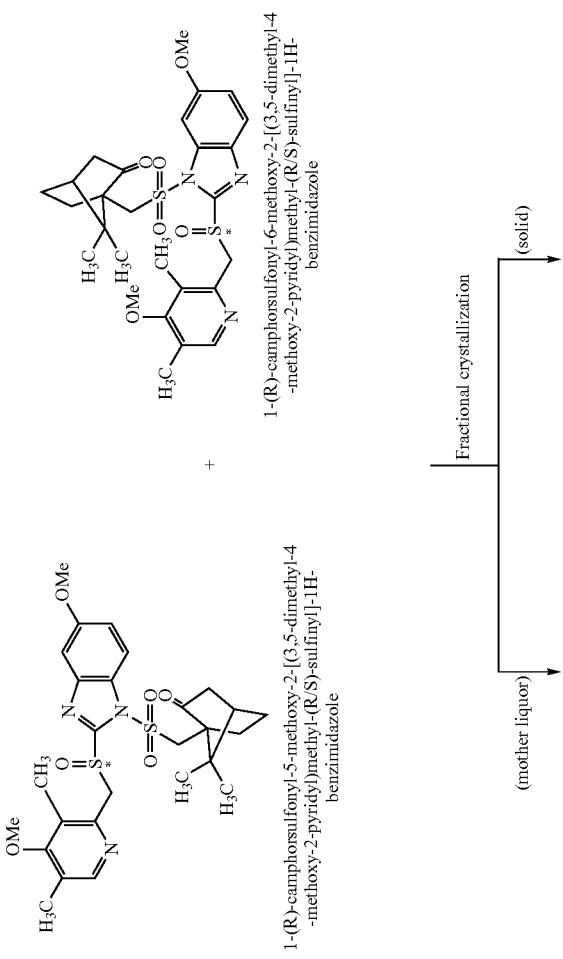

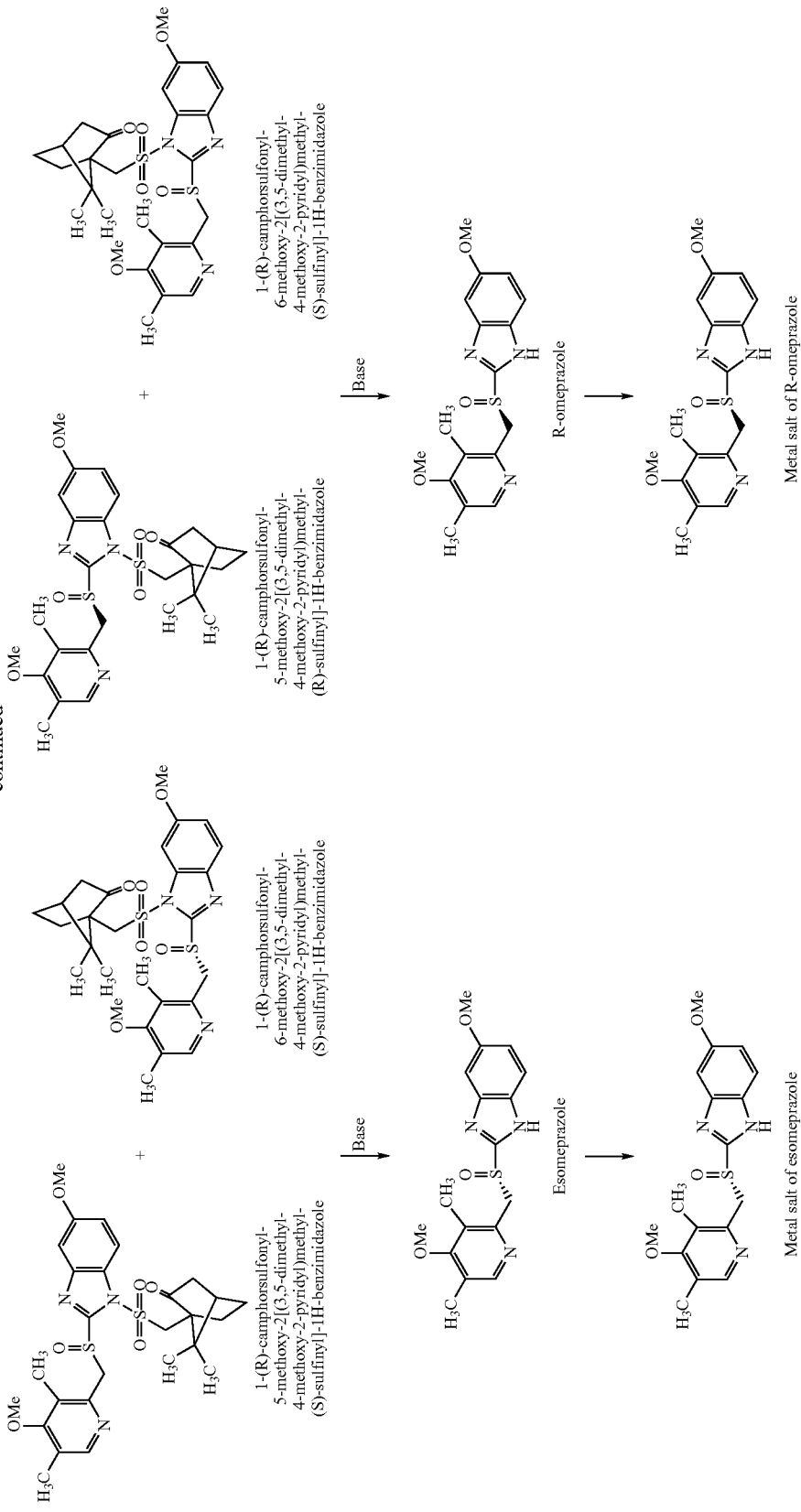

The diastereomers formed by reaction between 5-Methoxy-2-[(3,5-dimethyl-4-methoxy-2-pyridyl)methylthio]1-H-benzimidazole and (R)-camphor sulfonyl chloride results in the formation of a mixture of 1-(R)-camphor sulfonyl-(5- and 6-)-methoxy-2-[(3,5-dimethyl-4-methoxy-2-pyridyl) methylthio]-1H-benzimidazole, which is then oxidized to give a diastereomeric mixture of 1-(R)-camphorsulfonyl-(5- and 6-)-methoxy-2-[(3,5-dimethyl-4-methoxy-2-pyridyl) methyl-(R/S)-sulfinyl]-1H-benzimidazole. The diastereomeric compounds with 'S'-configuration at sulfur of sulfoxide group (i.e, 1-(R)-camphorsulfonyl-(5- and 6-)-methoxy-2-[(3,5-dimethyl-4-methoxy-2-pyridyl)methyl-(S)-sulfinyl]-1H-benzimidazole) are formed in excess over the diastereomeric compounds with 'R'-configuration at sulfur of sulfoxide group (i.e., 1-(R)-camphorsulfonyl-(5- and 6-)-methoxy-2-[(3,5-dimethyl-4-methoxy-2-pyridyl)methyl-(R)-sulfinyl]1H-benzimidazole). From the mixture of 5- and 6-methoxy-benzimidazoles thus obtained, those with one configuration at the sulfur atom of sulfoxide group are separated by fractional crystallization from those with the opposite configuration, followed by deprotection to give esomeprazole and R-omeprazole separately.

The formation of such 5- and 6- substituted benzimidazoles are common for example as mentioned in U.S. Pat. No. 5,714,504 and where applicable such a benzimidazole compounds of formula IV and diastereomers of the benzimidazole compounds of formula V; and the preparation of such compounds are also part of the invention.

Such a mixture of substituted benzimidazole compounds usually results from the presence of tautomeric forms of benzimidazole ring and they result when at least one of $R_1$ to $R_4$ is different from any of the rest of them provided if $R_1$ and $R_4$ are same, $R_2$ and $R_3$ are different; or if $R_2$ and $R_3$ are same, $R_1$ and $R_4$ are different. Even though these structures are not shown for the formulas IV and V for the sake of clarity, they are implied and also the part of the invention. The sequence of reactions and structures for these compounds can be shown as:

Scheme:

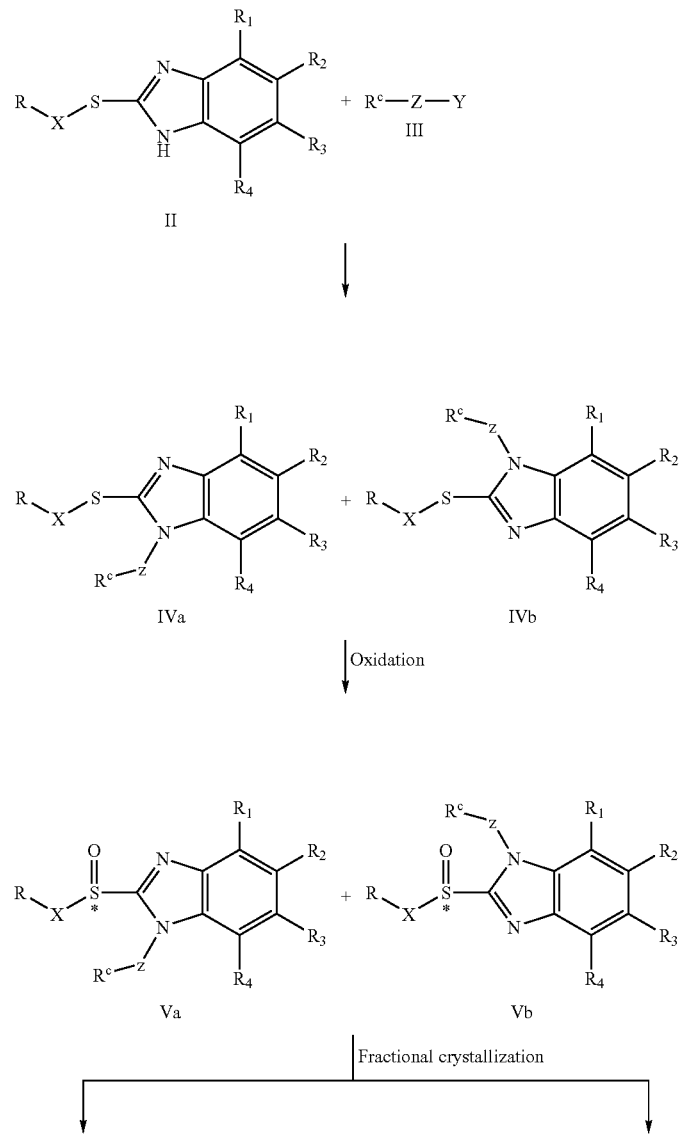

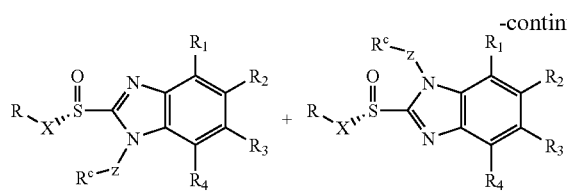
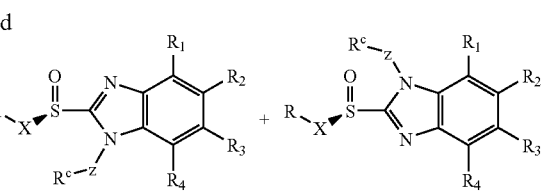
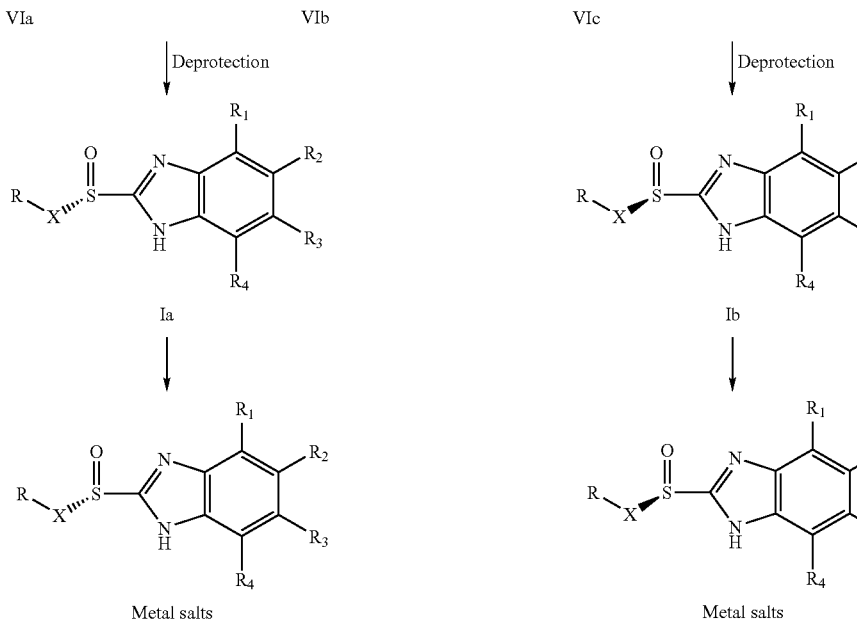

The compounds of formulas IVa, IVb and VIa to VId may be separated in to substantially pure compounds from their respective fractions by suitable means such as chromatographic techniques and/or fractional crystallization. For example, the individual isomers can be obtained by repeated crystallizations of alcoholic or ketonic solution or a mixture thereof from the mixture of IVa and IVb; VIa and VIb; or VIc and VId.

Any of the compounds of formulas IVa, IVb and VIa to VId in substantially pure form are novel and constitutes another aspect of the invention.

The individual compounds of formula IVa and IVb may also be used for preparing the compounds of formula I as a single enantiomer or in an enantiomerically enriched form by treating these compounds essentially the same manner as described for formula IV.

The individual isomers of the formula VIa to VId may also be used for preparing the compounds of formula I as a single enantiomer or in an enantiomerically enriched form by treating these isomers essentially the same manner as described for formula V.

Substantially pure refers to purity of the compound more than 85% of total of all the four isomers (i.e., VIa to VId), more preferably above 95% of total of all the four isomers and still more preferably above 98% of total of all the four isomers.

The following examples are given for the purpose of illustrating the present invention and should not be considered as limitations on the scope or spirit of the invention.

EXAMPLE 1

5-Methoxy-2-[(3,5-dimethyl-4-methoxy-2-pyridyl)methylthio]-1H-benzimidazole (15 gm) was dissolved in methylene chloride (150 ml) and N,N-diisopropylethylamine (9.0 gm) was added to the solution. The solution was cooled to 0° C.-5° C. (R)-Camphor sulfonyl chloride (14.0 gm) dissolved in 25 ml of methylene chloride was added slowly for one hour at 0° C.-5° C. The reaction mixture was maintained at 0° C.-5° C. for 3 hours. The pH was adjusted to 6.0-6.5 with acetic acid, then ice-cooled water (60 ml) was added. The layers were separated. The organic layer was washed with 10% aqueous sodium chloride. The organic layer was distilled under reduced pressure to obtain a residue containing the mixture of 1-(R)-camphor sulfonyl-5-methoxy-2-[(3,5-dimethyl-4-methoxy-2-pyridyl)methylthio]-1H-benzimidazole and 1-(R)-camphor sulfonyl-6-methoxy-2-[(3,5-dimethyl-4-methoxy-2-pyridyl)methylthio]-1H-benzimidazole (19.8 gm).

EXAMPLE 2

The residue (19.8 gm) obtained as in example 1 was mixed with methylene chloride (200 ml) at 30° C.-35° C., cooled to −5° C. and then the solution of m-chloro perbenzoic acid (8.0 gm) in methylene chloride (80 ml) was added drop wise for 30 minutes at −5° C. The contents were stirred for 3 hours at −5° C., then the reaction mass was filtered and washed with 5% NaHCO$_3$ (80 ml). The organic layer was dried and distilled to give the residue containing the diastereomeric mixture of 1-(R)-camphor sulfonyl-(5- and 6-)-methoxy-2-[(3,5-dimethyl-4-methoxy-2-pyridyl)methyl-(S)-sulfinyl]-1H-benzimidazole and 1-(R)-camphor sulfonyl-(5- and 6-)-methoxy-2-[(3,5-dimethyl-4-methoxy-2-pyridyl)methyl-(R)-sulfinyl]-1H-benzimidazole (18.0 gm) (the ratio of diastereomeric mixture of 1-(R)-camphor sulfonyl-(5- and 6-)-methoxy-2-[(3,5-dimethyl-4-methoxy-2-pyridyl)methyl-(S)-sulfinyl]-1H-benzimidazole and 1-(R)-camphor sulfonyl-(5- and 6-)-methoxy-2-[(3,5-dimethyl-4-methoxy-2-pyridyl)methyl-(R)-sulfinyl]-1H-benzimidazole was 4.4:1).

EXAMPLE 3

The residue (18.0 gm) obtained as in example 2 was stirred with isopropyl alcohol (50 ml) for 2 hours at 25° C. and then refluxed for 1 hour. The solution was cooled to 25° C. and maintained for 3 hours. The solid obtained was collected by filtration. The solid was stirred in methanol (80 ml) for 30 min and filtered to obtain a mixture of 1-(R)-camphor sulfonyl-5-methoxy-2-[(3,5-dimethyl-4-methoxy-2-pyridyl)methyl-(R)-sulfinyl]-1H-benzimidazole and 1-(R)-camphor sulfonyl-6-methoxy-2-[(3,5-dimethyl-4-methoxy-2-pyridyl)methyl-(R)-sulfinyl]-1H-benzimidazole as solid (3.5 gm).

EXAMPLE 4

Methanol (50 ml) was added to the product (3.5 gm) obtained as in example 2 and stirred for 30 min at 25° C., then sodium hydroxide solution (1 gm in 5 ml water) was added slowly for 10 min. The contents were stirred for 3 hours at 25° C. and then distilled to obtain a residue. To the residue was added water (25 ml), the pH was adjusted to 6.8 with acetic acid and the product was extracted with methylene chloride (3×50 ml). The layers were separated. The methylene chloride layer was washed with 5% aq. sodium chloride (25 ml), dried with sodium sulfate and the solvent was distilled to obtain 1.6 gm residue containing (R)-5-Methoxy-2-[(3,5-dimethyl-4-methoxy-2-pyridyl)methylsulfinyl]-1H-benzimidazole (R-omeprazole).

EXAMPLE 5

Treat the mother liquor (containing 1-(R)-camphor sulfonyl-(6- and 5-)-methoxy-2-[(3,5-dimethyl-4-methoxy-2-pyridyl)methyl-(S)-sulfinyl]-1H-benzimidazole in 3.2:1 ratio) from example 3 as follows:

The solvent was distilled to obtain a residue. The residue was dissolved in methylene chloride (100 ml) and washed with water (2×50 ml). The organic layer was distilled, methanol (80 ml) was added to the residue obtained and stirred for 30 min at 25° C. Then sodium hydroxide solution (3.0 gm in 10 ml water) was added slowly for 10 min. The contents were stirred for 3 hours at 25° C. Then methanol was distilled off to obtain a residue. To the residue was added water (50 ml), the pH was adjusted to 6.8 with acetic acid and the product was extracted with methylene chloride (3×50 ml). The layers were separated. The methylene chloride layer was washed with 5% aq. sodium chloride (50 ml), dried with sodium sulfate and the solvent was distilled to obtain 6.5 gm residue containing (S)-5-Methoxy-2-[(3,5-dimethyl-4-methoxy-2-pyridyl)methylsulfinyl]-1H-benzimidazole (Esomeprazole).

EXAMPLE 6

The residue (6.5 gm) obtained as in example 5 was dissolved in methanol (40 ml) at 25° C. and the solution was cooled to 5-10° C. Potassium hydroxide solution in methanol (2.0 gm in 10 ml methanol) was added slowly for 30 min. During addition of potassium hydroxide solution, solid was thrown out. The temperature was raised to 25° C., stirred for 14 hours, filtered and dried to obtain 6.2 gm of potassium salt of (S)-5-Methoxy-2-[(3,5-dimethyl-4-methoxy-2-pyridyl)methylsulfinyl]-1H-benzimidazole (Esomeprazole potassium) (Enantiomeric excess: 99.4%).

EXAMPLE 7

Potassium salt of (S)-5-Methoxy-2-[(3,5-dimethyl-4-methoxy-2-pyridyl)methylsulfinyl]-1H-benzimidazole (Esomeprazole potassium) (6.2 gm) was dissolved in water (80 ml). To this solution, was added magnesium chloride solution (1.8 gm in 50 ml water), and then the contents were stirred for 1 hour at 25° C. The solid precipitated was filtered, washed with water and dried under vacuum for 12 hours at 40° C. to obtain 4.5 gm of esomeprazole magnesium dihydrate (enantiomeric excess: 99.5%).

We claim:

1. A substantially pure compound of formula VIa to VId:

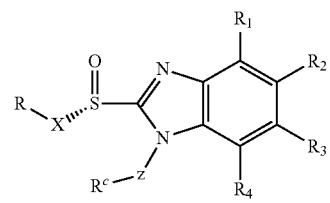

VIa

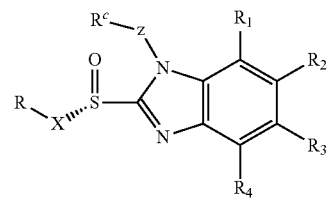

VIb

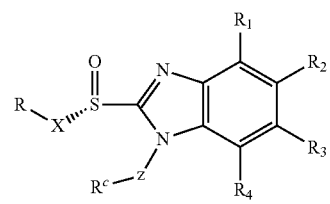

VIc

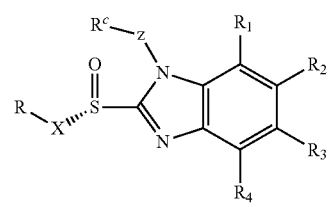

VId wherein R is

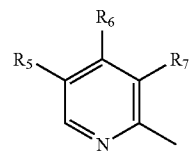 or 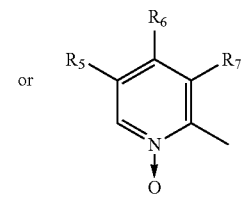

X is

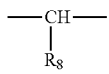

and

R₁-R₄ are the same or different and selected from hydrogen, alkyl, alkoxy, halogen, halo-alkoxy, alkylcarbonyl, alkoxycarbonyl, trifluroalkyl;

wherein

R₅ and R₇ are same or different and selected from hydrogen, alkyl, alkylthio, alkoxy optionally substituted by fluorine, alkoxyalkoxy, dialkylamino, halogen, phenylalkyl and phenylalkoxy;

R₆ is selected from hydrogen, alkyl, alkylthio, alkoxy optionally substituted by fluorine, alkoxyalkoxy, dialkylamino, halogen, nitro, phenylalkyl and phenylalkoxy;

R₈ is hydrogen or forms an alkylene chain together with R₇;

R$^C$—Z— is selected from (S) or (R)-camphor sulfonyl, (S)- or (R)-glycidylsulfonyl-, D- or L-mandeloyl, a stereo isomeric 1-(ethoxycarbonyl)-3-phenylpropylalanyl, (D) or (L)-phenyl alanyl and (D) or (L)-alanyl; with the proviso that at least one of R₁ to R₄ is different from any of the rest of them provided if R₁ and R₄ are same, R₂ and R₃ are different; or if R₂ and R₃ are same, R₁ and R₄ are different.

2. The compound of claim 1, wherein R is

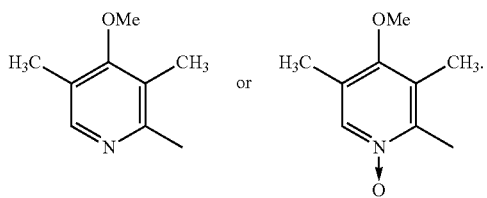

3. The compound of claim 1, wherein X is —CH2.

4. The compound of formula VIa to VId of claim 1, wherein R is

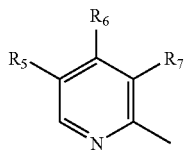

R₁=R₃=R₄=H; R₂ is —OCH3 and X is —CH2.

5. The compound of any of claims 1 to 4, wherein Z is

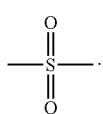

6. The compound of claim 1, wherein Rc—Z— is (S) or (R)-camphor sulfonyl.

7. The compound of claim 6, wherein Rc—Z— is (R)-camphor sulfonyl.

8. A Benzimidazole sulfide of formula IV:

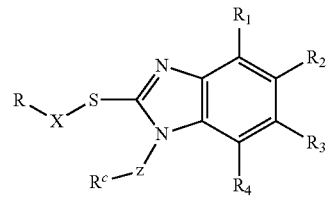

wherein R is

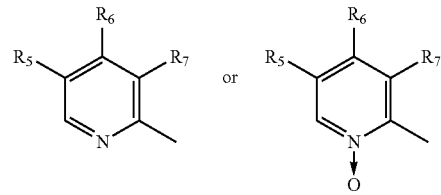

X is

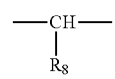

and

R₁-R₄ are the same or different and selected from hydrogen, alkyl, alkoxy, halogen, halo-alkoxy, alkylcarbonyl, alkoxycarbonyl, trifluroalkyl;

wherein

R₅ and R₇ are same or different and selected from hydrogen, alkyl, alkylthio, alkoxy optionally substituted by fluorine, alkoxyalkoxy, dialkylamino, halogen, phenylalkyl and phenylalkoxy;

R₆ is selected from hydrogen, alkyl, alkylthio, alkoxy optionally substituted by fluorine, alkoxyalkoxy, dialkylamino, halogen, nitro, phenylalkyl and phenylalkoxy;

R₈ is hydrogen or forms an alkylene chain together with R₇;

R$^c$—Z— is selected from (S) or (R)-camphor sulfonyl, (S)- or (R)-glycidylsulfonyl-, D- or L-mandeloyl, a stereo isomeric 1-(ethoxycarbonyl)-3-phenylpropylalanyl, (D) or (L)-phenyl alanyl and (D) or (L)-alanyl; with the proviso that at least one of R₁ to R₄ is different from any of the rest of them provided if R₁ and R₄ are same, R₂ and R₃ are different; or if R₂ and R₃ are same, R₁ and R₄ are different.

9. The compound of claim 8, wherein X is —CH₂ and R is

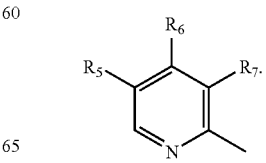

10. The compound of claim 8, wherein R is

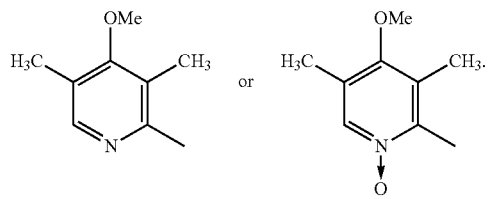

$R_1=R_3=R_4=H$; $R_2$ is —$CH_3$ and X is —$CH_2$.

11. The compound of any of claims 8 to 10, wherein Z is

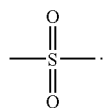

12. The compound of claim 8, wherein $R^c$—Z— is (S) or (R)-camphor sulfonyl.

13. The compound of claim 12, wherein $R^c$—Z— is (R)-camphor sulfonyl.

14. A compound of formula IVa and IVb in substantially pure form:

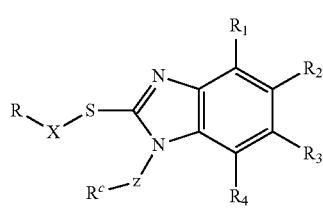
IVa

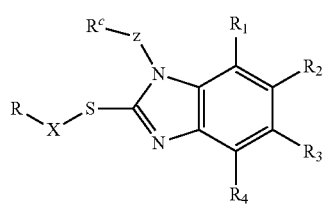
IVb wherein R is

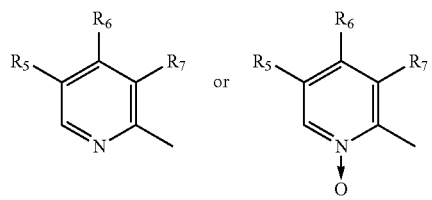

X is

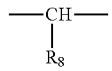

and $R_1$-$R_4$ are the same or different and selected from hydrogen, alkyl, alkoxy, halogen, halo-alkoxy, alkylcarbonyl, alkoxycarbonyl, trifluroalkyl;

wherein $R_5$ and $R_7$ are same or different and selected from hydrogen, alkyl, alkylthio, alkoxy optionally substituted by fluorine, alkoxyalkoxy, dialkylamino, halogen, phenylalkyl and phenylalkoxy;

$R_6$ is selected from hydrogen, alkyl, alkylthio, alkoxy optionally substituted by fluorine, alkoxyalkoxy, dialkylamino, halogen, nitro, phenylalkyl and phenylalkoxy;

$R_8$ is hydrogen or forms an alkylene chain together with $R_7$;

$R^c$—Z— is selected from (S) or (R)-camphor sulfonyl, (S)- or (R)-glycidylsulfonyl-, D- or L-mandeloyl, a stereo isomeric 1-(ethoxycarbonyl)-3-phenylpropylalanyl, (D) or (L)-phenyl alanyl and (D) or (L)-alanyl; with the proviso that at least one of $R_1$ to $R_4$ is different from any of the rest of them provided if $R_1$ and $R_4$ are same, $R_2$ and $R_3$ are different; or if $R_2$ and $R_3$ are same, $R_1$ and $R_4$ are different.

15. The compound of claim 14, wherein X is —$CH_2$ and R is

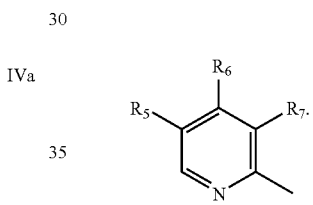

16. The compound of claim 14, wherein R is

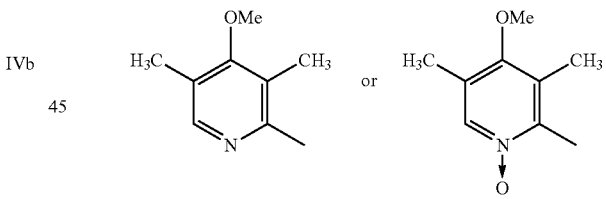

$R_1=R_3=R_4=H$; $R_2$ is —$OCH_3$ and X is —$CH_2$.

17. The compound of any of claims 14 to 16, wherein Z is

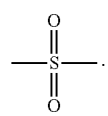

18. The compound of claim 14, wherein $R^c$—Z— is (S) or (R)-camphor sulfonyl.

19. The compound of claim 18, wherein $R^c$—Z— is (R)-camphor sulfonyl.

* * * * *